(12) United States Patent  
Ma et al.

(10) Patent No.: US 9,282,904 B2
(45) Date of Patent: Mar. 15, 2016

(54) PORTABLE DETECTING DEVICE WITH TWO ELECTRODES

(71) Applicant: Shenzhen Breo Technology Co., Ltd., Shenzhen (CN)

(72) Inventors: Xuejun Ma, Shenzhen (CN); Chuanle Jiang, Shenzhen (CN)

(73) Assignee: Shenzhen Breo Technology Co., Ltd., Shenzhen (CN)

( * ) Notice: Subject to any disclaimer, the term of this patent is extended or adjusted under 35 U.S.C. 154(b) by 0 days.

(21) Appl. No.: 14/356,026

(22) PCT Filed: Dec. 23, 2013

(86) PCT No.: PCT/CN2013/090228
§ 371 (c)(1),
(2) Date: May 2, 2014

(87) PCT Pub. No.: WO2015/096003
PCT Pub. Date: Jul. 2, 2015

(65) Prior Publication Data
US 2015/0173632 A1 Jun. 25, 2015

(51) Int. Cl.
*A61B 5/04* (2006.01)
*A61B 5/024* (2006.01)
*A61B 5/1455* (2006.01)
*A61B 5/0245* (2006.01)
*A61B 5/0428* (2006.01)
*A61B 5/00* (2006.01)

(52) U.S. Cl.
CPC ........... *A61B 5/02438* (2013.01); *A61B 5/0245* (2013.01); *A61B 5/0428* (2013.01); *A61B 5/14552* (2013.01); *A61B 5/681* (2013.01)

(58) Field of Classification Search
CPC ............. A61B 5/0295; A61B 5/02438; A61B 5/0402; A61B 5/681; A61B 5/02427; A61B 5/02125

See application file for complete search history.

(56) References Cited

U.S. PATENT DOCUMENTS

2012/0194976 A1 8/2012 Golko et al.
2014/0358012 A1* 12/2014 Richards et al. .............. 600/479

FOREIGN PATENT DOCUMENTS

CN 1965286 5/2007
CN 203311163 11/2013

OTHER PUBLICATIONS

International Search Report for PCT/CN2013/090228, dated Sep. 29, 2014 (2 pages total).

* cited by examiner

*Primary Examiner* — Robert N Wieland
(74) *Attorney, Agent, or Firm* — Hamre, Schumann, Mueller & Larson, P.C.

(57) ABSTRACT

The invention is suitable for the communication and electron field, and provides a portable detecting device with two electrodes, the portable detecting device comprises: a main body of the portable detecting device and a wrist strap, wherein the main body of the portable detecting device comprises: a front and a back, wherein the front comprises a first lead electrode detecting a finger signal; and the back comprises a second lead electrode detecting a wrist signal. The technical solution provided by the present invention has the advantage of convenient for users to carry and easy for users obtaining the data thereof.

9 Claims, 7 Drawing Sheets

PORTABLE DETECTING DEVICE WITH TWO ELECTRODES

TECHNICAL FIELD

The present invention relates to electron and communication field, and more particularly, to a portable detecting device with two electrodes.

BACKGROUND

With the development of the mobile technology, many traditional electronic products begin to be added functions of mobility. For example, the watch that was only used to inform the time, now can be connected to the internet through the smart phone or the home network to display incoming calls information, twitter and news feeds, and weather information and so on.

This new watches are called smart watch, some of them are sold on the market, and some of them are in the sample testing stage. This kind of product is designed for consumers to use in the case that the consumers are not convenient to use the intelligent mobile phone, for example when the consumers are riding a bike or carrying many things in the hand.

The concept of smart watch had appeared at least before 2000: Microsoft launched such a product in 2003. Many companies have started selling this kind of products, including Sony, Pebble developed by financing channel and Italian company i'm.

Sony "SmartWatch"

This kind of product needs to be used with Sony Xperia, and also can be compatible with most of the Android mobile phone based on the Android system version 2.1 and above. This kind of smart phone has a color touch screen, original wristband is black rubber wristband, five different shapes of wristbands also may be chosen.

Because such smart watch needs to receive information from the mart phone, the smart watch can't be apart from the smart phone for too long. Bluetooth wireless communication distance between the watch and smart phones is about 30 feet. This watch has no sound function, but it is equipped with a vibration alert function, and it is not easy for the consumers to miss the received short message. In addition, this smart watch has no input function, and can only send some preset simple reply, such as "busy now" and so on. The used e-mail program of the smart watch is Gmail, but e-mail attachments can not be read on the watch. SmartWatch requires two applications to be set, namely LiveWare Manager and SmartWatch, these two applications can be downloaded for free from Google Play. Most Xperia phones are preloaded with LiveWare program.

WIMM One

A company called WIMM Labs in Los Altos, Calif. also introduced a similar smart watches called WIMM One, the product is mainly designed for developers. WIMM One is slightly larger than Sony's SmartWatch, built more powerful processors and two wireless communication function, Bluetooth and WiFi, so it can work through the home network. WIMM One can be used for 30 hours on one charge. The smart watch is preloaded six applications, users can also download more free apps from WIMM Micro App Store Beta.

Smart Watch Pebble

A company called Allerta in American released a new smart watch Pebble, this is their second product since Pulse's was launched in 2009. The smart "selling point" of Pebble is that it can be communicated with your iPhone or Android phone via Bluetooth, as long as a telephone, SMS comes in, the watch will vibrate to remind the user timely, also the messages, weather and schedule may be checked in the watch.

The technical solution in the prior art has the following technical problem:

the terminal equipment provided by the prior art can only achieve a very simple reminder function, and is unable to detect the user's body data (such as heart rate and blood oxygen content and other indices).

SUMMARY

The present invention aims at providing a portable detecting device with two electrodes to solve the problem that the smart watch in the prior art can't detect the user's body data.

In a first aspect, the embodiment of the present invention is achieved by providing a portable detecting device with two electrodes, the device comprises: a main body of the portable detecting device and a wrist strap, wherein the main body of the portable detecting device comprises: a front and a back, wherein the front comprises a first lead electrode detecting a finger signal; and the back comprises a second lead electrode detecting a wrist signal.

Combined with the technical solution of the first aspect, in a first alternative of the first aspect, the first lead electrode comprises: a finger composite detecting probe and an optical module.

Combined with the first alternative of the first aspect, in a second alternative of the first aspect, the portable detecting device further comprises a detecting circuit, the detecting circuit comprises: an amplifier, a microcontroller unit and a switching element; wherein a detecting signal of the optical module is connected to the microcontroller unit through the amplifier; and a detecting signal of the finger composite detecting probe and a detecting signal of the second lead electrode are connected to the microcontroller unit through the amplifier.

Combined with the second alternative of the first aspect, in a third alternative of the first aspect, the detecting circuit specifically comprises:

a first amplifier, a second amplifier, a third amplifier, a microcontroller unit (MCU) and a field effect transistor, wherein:

a negative terminal of the first amplifier is connected to an output terminal of the first amplifier, the output terminal of the first amplifier is connected to the MCU, a positive terminal of the first amplifier is connected to the detecting signal of the optical module;

a negative terminal of the second amplifier is connected to an output terminal of the second amplifier, the output terminal of the second amplifier is connected to the MCU, a positive terminal of the second amplifier is connected to the detecting signal of the finger composite detecting probe;

a negative terminal of the third amplifier is connected to an output terminal of the third amplifier, the output terminal of the third amplifier is connected to the MCU, a positive terminal of the third amplifier is connected to the detecting signal of the second lead electrode; the detecting signal of the second lead electrode is connected to a drop terminal D of the field effect transistor, a source terminal S of the field effect transistor is connected to the ground, and a gate terminal G of the field effect transistor is connected to the MCU.

Combined with the second alternative of the first aspect, in a fourth alternative of the first aspect, the detecting circuit specifically comprises:

a first amplifier, a second amplifier, a third amplifier, a microcontroller unit (MCU) and a field effect transistor, wherein:

a negative terminal of the first amplifier is connected to an output terminal of the first amplifier, the output terminal of the first amplifier is connected to the MCU, a positive terminal of the first amplifier is connected to the detecting signal of the optical module;

a negative terminal of the second amplifier is connected to an output terminal of the second amplifier, the output terminal of the second amplifier is connected to the MCU, a positive terminal of the second amplifier is connected to the detecting signal of the finger composite detecting probe;

a negative terminal of the third amplifier is connected to an output terminal of the third amplifier, the output terminal of the third amplifier is connected to the MCU, a positive terminal of the third amplifier is connected to a source terminal S of the field effect transistor; a drop terminal D of the field effect transistor is connected to the detecting signal of the second lead electrode, and a gate terminal G of the field effect transistor is connected to the MCU.

Combined with the second alternative of the first aspect, in a fifth alternative of the first aspect, the detecting circuit specifically comprises:

a first amplifier, a second amplifier, a third amplifier, a microcontroller unit (MCU) and a field effect transistor, wherein:

a negative terminal of the first amplifier is connected to an output terminal of the first amplifier, the output terminal of the first amplifier is connected to the MCU, a positive terminal of the first amplifier is connected to the detecting signal of the optical module;

a negative terminal of the second amplifier is connected to an output terminal of the second amplifier, the output terminal of the second amplifier is connected to the MCU, a positive terminal of the second amplifier is connected to the detecting signal of the finger composite detecting probe; the detecting signal of the finger composite detecting probe is connected to a drop terminal D of the field effect transistor, a source terminal S of the field effect transistor is connected to the ground, and a gate terminal G of the field effect transistor is connected to the MCU;

a negative terminal of the third amplifier is connected to an output terminal of the third amplifier, the output terminal of the third amplifier is connected to the MCU, a positive terminal of the third amplifier is connected to the detecting signal of the second lead electrode.

Combined with the second alternative of the first aspect, in a sixth alternative of the first aspect, the detecting circuit specifically comprises:

a first amplifier, a second amplifier, a third amplifier, a microcontroller unit (MCU) and a field effect transistor, wherein:

a negative terminal of the first amplifier is connected to an output terminal of the first amplifier, the output terminal of the first amplifier is connected to the MCU, a positive terminal of the first amplifier is connected to the detecting signal of the optical module;

a negative terminal of the second amplifier is connected to an output terminal of the second amplifier, the output terminal of the second amplifier is connected to the MCU, a positive terminal of the second amplifier is connected to a source terminal S of the field effect transistor, a drop terminal D of the field effect transistor is connected to the detecting signal of the finger composite detecting probe, and a gate terminal G of the field effect transistor is connected to the MCU a negative terminal of the third amplifier is connected to an output terminal of the third amplifier, the output terminal of the third amplifier is connected to the MCU, a positive terminal of the third amplifier is connected to the detecting signal of the second lead electrode.

Combined with the second alternative, the third alternative, the fourth alternative or the sixth alternative of the first aspect, in a seventh alternative of the first aspect, the detecting circuit further comprises: a wireless transmitting module, the wireless transmitting module is connected to the MCU.

In the embodiments of the present invention, the technical solution of the present invention has the advantages that the users are easy to bring the smart swatch and it is convenient for the users to obtain the data in the swatch.

DETAILED DESCRIPTION OF THE PREFERRED EMBODIMENTS

To make the objectives, technical solutions and advantages of the present invention clearer, the present invention will be further described hereafter with reference to the accompany drawings and embodiments. However, it shall be understood that, the embodiments described herein are only intended to illustrate but not to limit the present invention.

Figure 1:
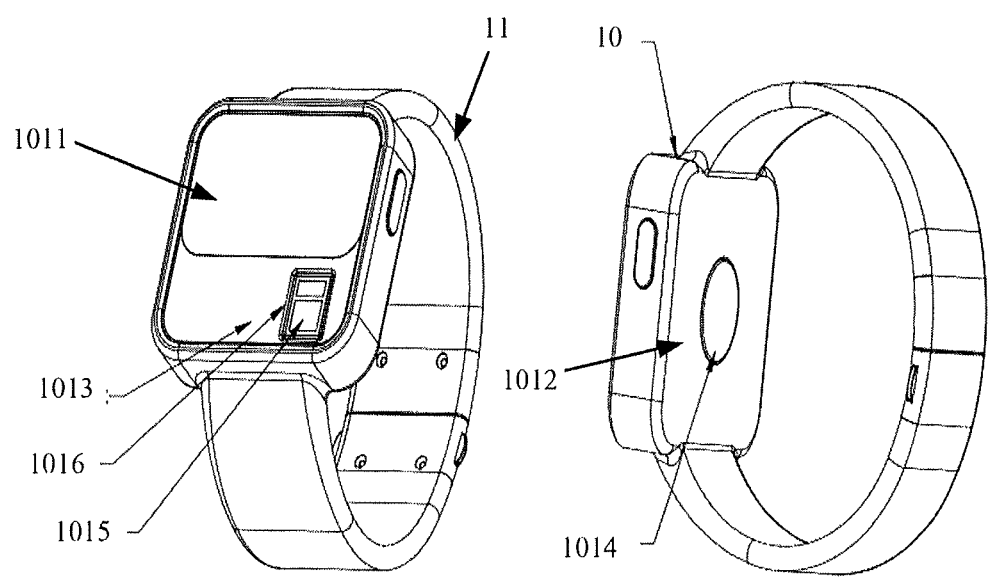
FIG. 1 is a schematic stereogram of a portable detecting device with two electrodes of the present invention.

A specific embodiment of the present invention provides a portable detecting device with two electrodes. The device is shown in FIG. 1, and comprises a main body 10 of the portable detecting device and a wrist strap 11; wherein the main body 10 of the portable detecting device comprises: a front 1011 and a back 1012, wherein the front 1011 comprises a first lead electrode 1013 detecting a finger signal; and the back 1012 comprises a second lead electrode 1014 detecting a wrist signal.

In the technical solution of the present invention, the portable device, that is the smart swatch, is provided with two lead electrodes which are respectively the finger signal lead electrode disposed on the front and the wrist lead electrode disposed on the back, such that after the user wears the smart swatch on the wrist, when one finger of a hand touches the finger signal lead electrode, the signals of the two lead electrodes pass through the heart of the user to achieve the purpose of detecting the heart rate and blood oxygen. Thus it is very convenient for such device detects the heart rate and blood oxygen in real time, and the device has the advantages that the users are easy to bring the smart swatch and it is convenient for the users to obtain the data in the swatch.

Alternatively, the first lead electrode 1013 comprises: a finger composite detecting probe 1016 and an optical module 1015.

Figure 7:
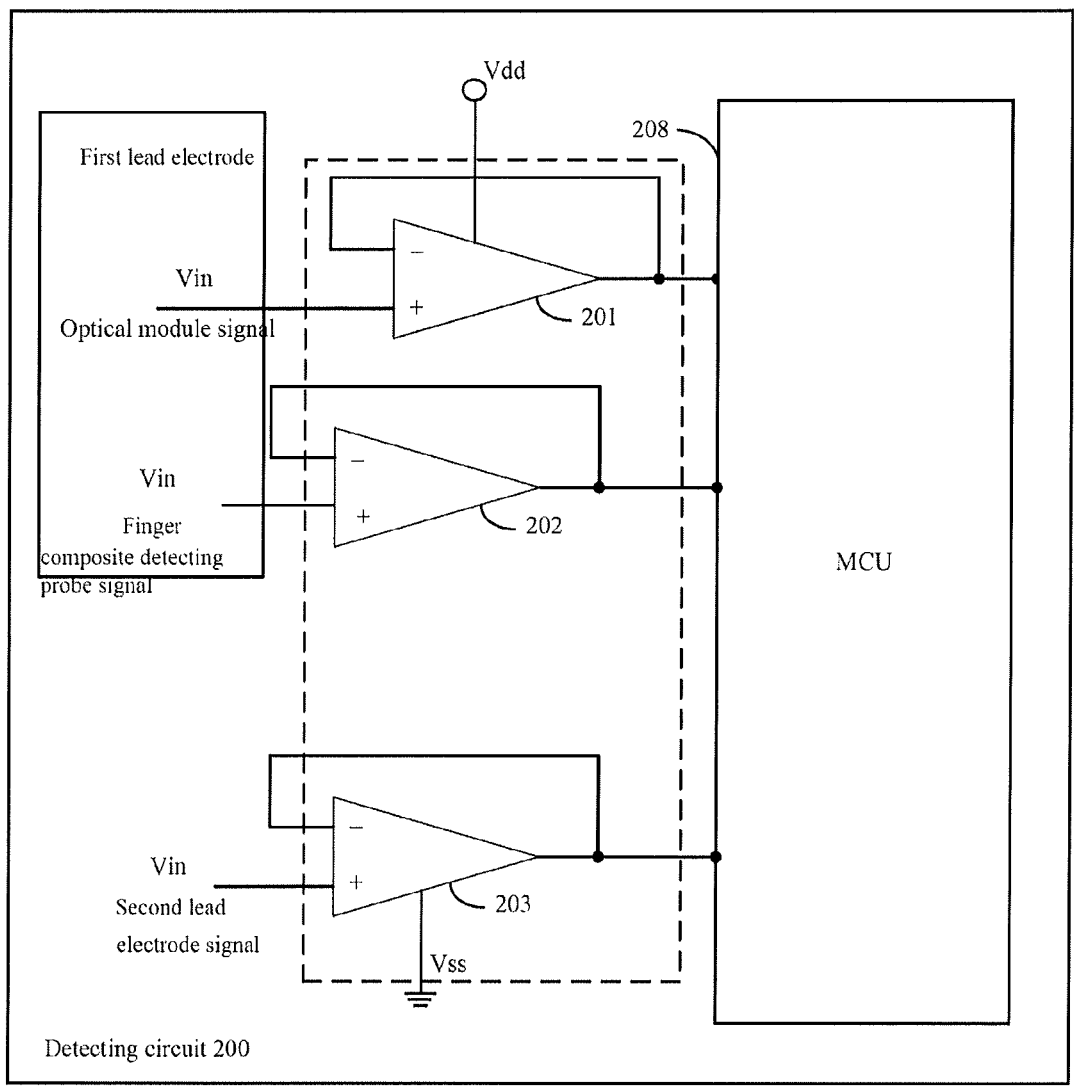
FIG. 7 is a circuit diagram of a fifth portable detecting device with two electrodes of the present invention.

Alternatively, the portable detecting device with two electrodes further comprises a detecting circuit 200, the detecting circuit 200 comprises:

a detecting signal of the optical module 1015 is connected to the microcontroller unit (MCU) through the amplifier; and a detecting signal of the finger composite detecting probe 1016 and a detecting signal of the second lead electrode 1014 are connected to the microcontroller unit (MCU) through the amplifier (no switching element is needed, the specific circuit is shown in FIG. 7).

Alternatively, that "a detecting signal of the finger composite detecting probe 1016 and a detecting signal of the second lead electrode 1014 are connected to the microcontroller unit (MCU) through the amplifier" may specifically comprises:

the detecting signal of the finger composite detecting probe 1016 or one detecting signal of the detecting signals of the second lead electrode 1014 is connected to the microcontroller unit (MCU) through the amplifier and the switching element; the detecting signal of the finger composite detecting probe 1016 or another detecting signal of the detecting signals of the second lead electrode 1014 is connected to the microcontroller unit (MCU) through the amplifier and the switching element.

It should be note that adding the switching element to the detecting circuit is to prevent the static electricity on the probe, because in the solution shown in FIG. 7 has no switching element connected to the ground, the first lead electrode in FIG. 7 is in no connection state, the probe may store some electrostatic charges if the probe in the no connection state for a long time. Then if the user wants to detect the information, the detected data is not correct due to the electrostatic chare. Adding the switching element connects the first electrode to the ground, when the first electrode is not working, and the electrostatic charge is not stored. Therefore the user may use the first electrode directly when detecting a signal, which avoids the electrostatic charge affecting the detecting result.

Figure 2:
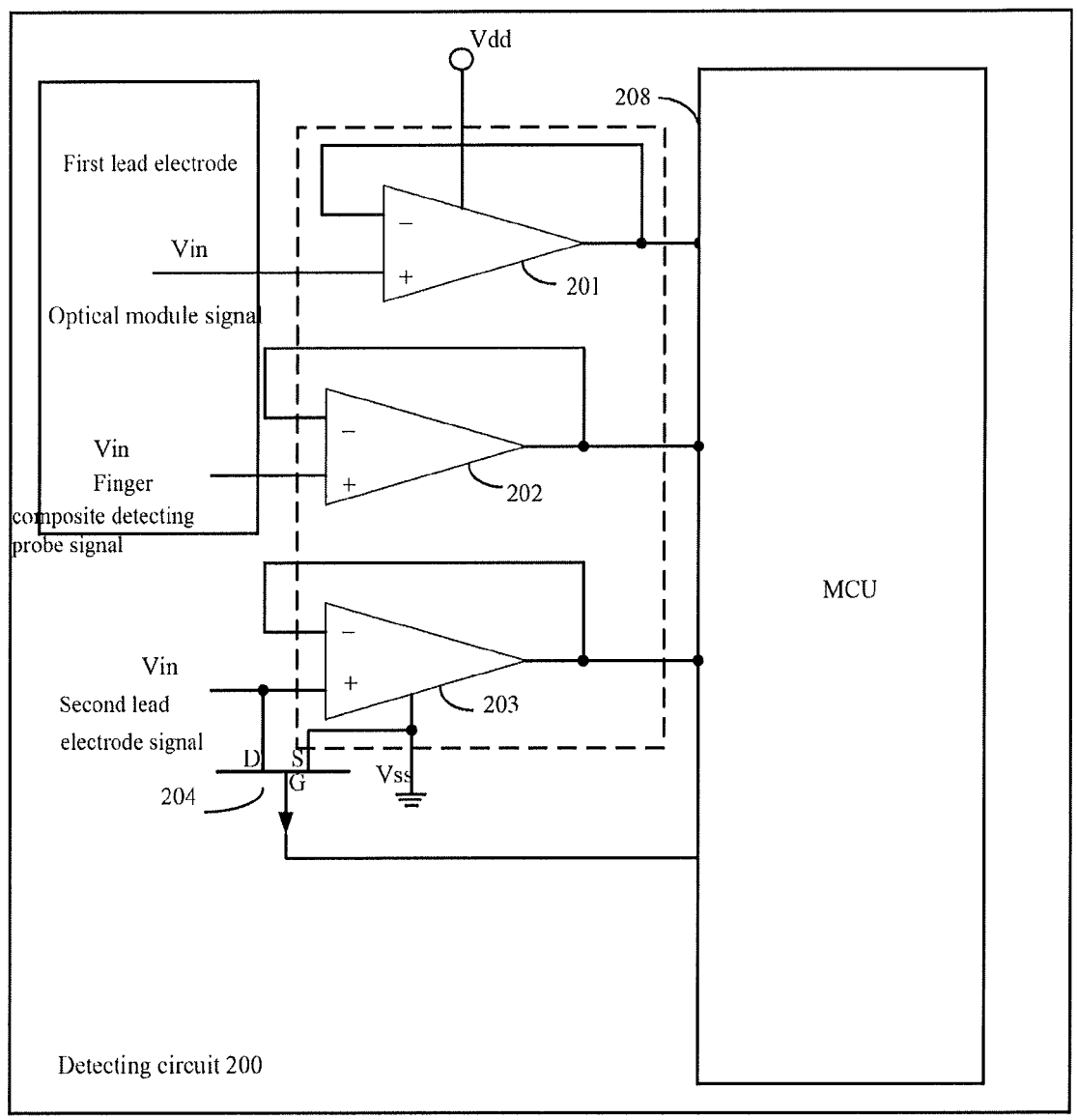
FIG. 2 is a circuit diagram of a first portable detecting device with two electrodes of the present invention.

Alternatively, a first alternative embodiment of the detecting circuit shown in FIG. 2, the detecting circuit comprises:

a first amplifier 201, a second amplifier 202, a third amplifier 203, a microcontroller unit (MCU) 208 and a field effect transistor 204, wherein:

a negative terminal of the first amplifier 201 is connected to an output terminal of the first amplifier 201, the output terminal of the first amplifier 201 is connected to the MCU 208, a positive terminal of the first amplifier 201 is connected to the detecting signal of the optical module 1015;

a negative terminal of the second amplifier 202 is connected to an output terminal of the second amplifier 202, the output terminal of the second amplifier 202 is connected to the MCU 208, a positive terminal of the second amplifier 202 is connected to the detecting signal of the finger composite detecting probe 1016;

a negative terminal of the third amplifier 203 is connected to an output terminal of the third amplifier 203, the output terminal of the third amplifier 203 is connected to the MCU 208, a positive terminal of the third amplifier 203 is connected to the detecting signal of the second lead electrode 1014; the detecting signal of the second lead electrode 1014 is connected to a drop terminal D of the field effect transistor 204, a source terminal S of the field effect transistor 204 is connected to the ground, and a gate terminal G of the field effect transistor 204 is connected to the MCU 208.

Figure 3:
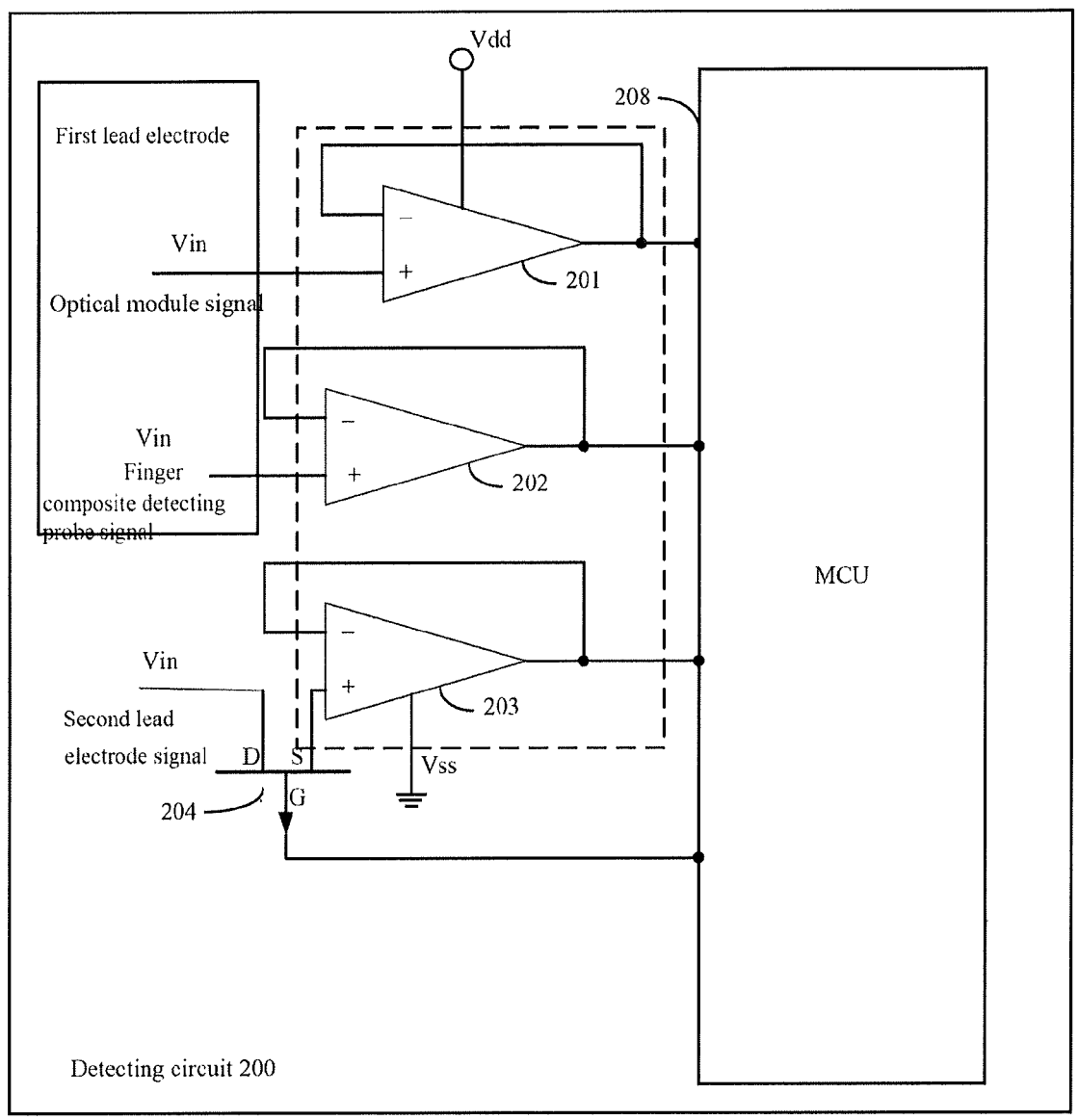
FIG. 3 is a circuit diagram of a second portable detecting device with two electrodes of the present invention.

Alternatively, a second alternative embodiment of the detecting circuit shown in FIG. 3, the detecting circuit comprises:

a first amplifier 201, a second amplifier 202, a third amplifier 203, a microcontroller unit (MCU) 208 and a field effect transistor 204, wherein:

a negative terminal of the first amplifier 201 is connected to an output terminal of the first amplifier 201, the output terminal of the first amplifier 201 is connected to the MCU 208, a positive terminal of the first amplifier 201 is connected to the detecting signal of the optical module 1015;

a negative terminal of the second amplifier 202 is connected to an output terminal of the second amplifier 202, the output terminal of the second amplifier 202 is connected to the MCU 208, a positive terminal of the second amplifier 202 is connected to the detecting signal of the finger composite detecting probe 1016;

a negative terminal of the third amplifier 203 is connected to an output terminal of the third amplifier 203, the output terminal of the third amplifier 203 is connected to the MCU 208, a positive terminal of the third amplifier 203 is connected to a source terminal S of the field effect transistor 204; a drop terminal D of the field effect transistor 204 is connected to the detecting signal of the second lead electrode 1014, and a gate terminal G of the field effect transistor 204 is connected to the MCU 208.

Figure 4:
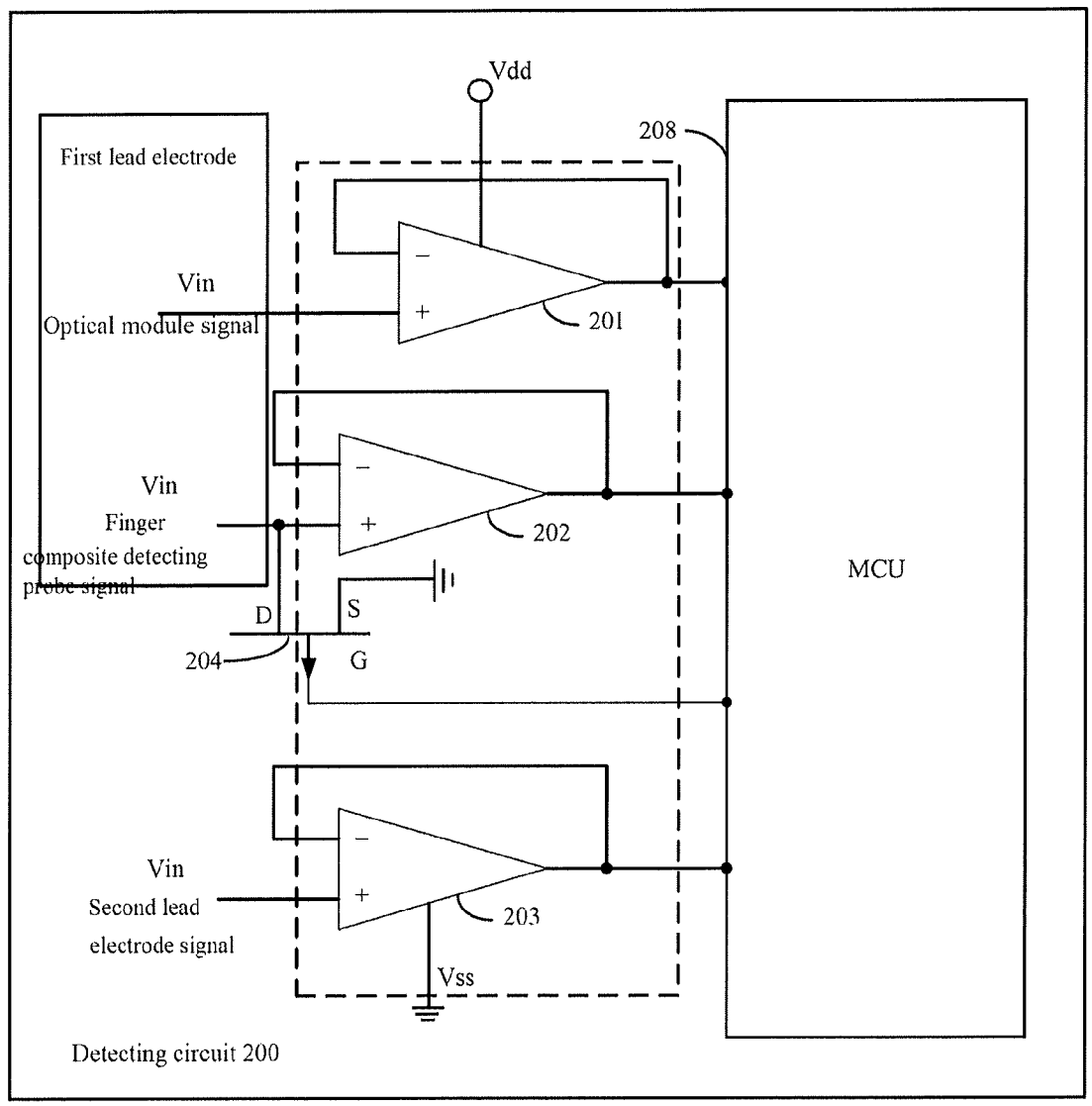
FIG. 4 is a circuit diagram of a third portable detecting device with two electrodes of the present invention.

Alternatively, a third alternative embodiment of the detecting circuit shown in FIG. 4, the detecting circuit comprises:

a first amplifier 201, a second amplifier 202, a third amplifier 203, a microcontroller unit (MCU) 208 and a field effect transistor 204, wherein:

a negative terminal of the first amplifier 201 is connected to an output terminal of the first amplifier 201, the output terminal of the first amplifier 201 is connected to the MCU 208, a positive terminal of the first amplifier 201 is connected to the detecting signal of the optical module 1015;

a negative terminal of the second amplifier 202 is connected to an output terminal of the second amplifier 202, the output terminal of the second amplifier 202 is connected to the MCU 208, a positive terminal of the second amplifier 202 is connected to the detecting signal of the finger composite detecting probe 1016; the detecting signal of the finger composite detecting probe 1016 is connected to a drop terminal D of the field effect transistor 204, a source terminal S of the field effect transistor 204 is connected to the ground, and a gate terminal G of the field effect transistor is connected to the MCU 208;

a negative terminal of the third amplifier 203 is connected to an output terminal of the third amplifier 203, the output terminal of the third amplifier 203 is connected to the MCU 208, a positive terminal of the third amplifier 203 is connected to the detecting signal of the second lead electrode 1014.

Figure 5:
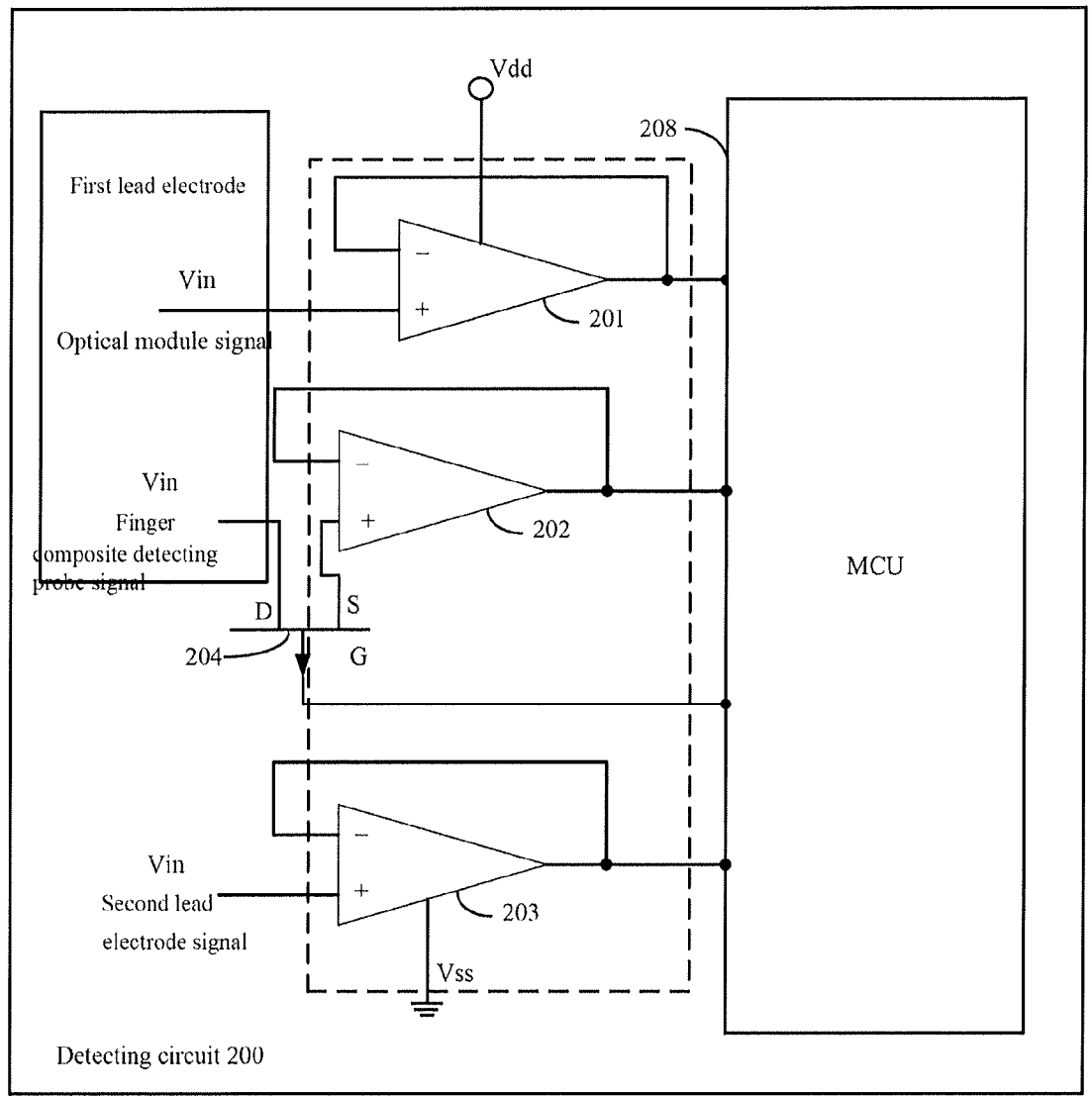
FIG. 5 is a circuit diagram of a fourth portable detecting device with two electrodes of the present invention.

Alternatively, a fourth alternative embodiment of the detecting circuit shown in FIG. 5, the detecting circuit comprises:

a first amplifier 201, a second amplifier 202, a third amplifier 203, a microcontroller unit (MCU) 208 and a field effect transistor 204, wherein:

a negative terminal of the first amplifier 201 is connected to an output terminal of the first amplifier 201, the output terminal of the first amplifier 201 is connected to the MCU 208, a positive terminal of the first amplifier 201 is connected to the detecting signal of the optical module 1015;

a negative terminal of the second amplifier 202 is connected to an output terminal of the second amplifier 202, the output terminal of the second amplifier 202 is connected to the MCU 208, a positive terminal of the second amplifier 202 is connected to a source terminal S of the field effect transistor 204, a drop terminal D of the field effect transistor 204 is connected to the detecting signal of the finger composite detecting probe 1016, and a gate terminal G of the field effect transistor 204 is connected to the MCU 208;

a negative terminal of the third amplifier 203 is connected to an output terminal of the third amplifier 203, the output terminal of the third amplifier 203 is connected to the MCU 208, a positive terminal of the third amplifier 203 is connected to the detecting signal of the second lead electrode 1014.

Alternatively, the detecting circuit 200 further comprises: a wireless transmitting module, the wireless transmitting module is connected to the MCU 208. The wireless transmitting module is responsible for wireless data transmission function, and may be the Bluetooth, wireless fidelity, or RF module and so on.

Figure 6:
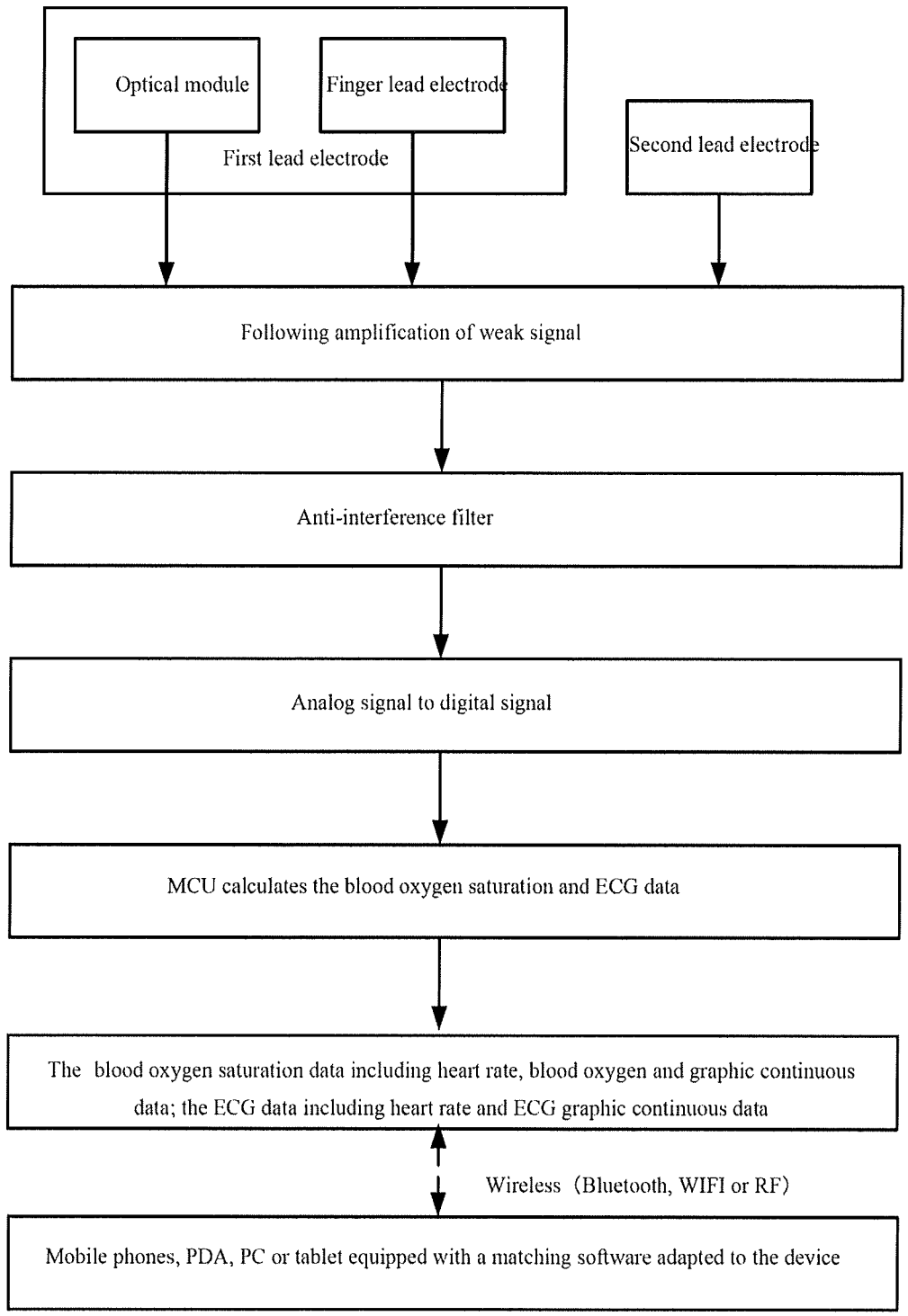
FIG. 6 is a flowchart of a implementing method for a portable detecting device of the present invention.

The implementation process of the technical solution of the present invention is shown in FIG. 6, wherein the detecting signals of the optical module, finger lead electrode and wrist lead electrode are amplified and transmitted to the MCU after anti-interference filter and analog to digital conversion procedure. The MCU calculates the blood oxygen saturation and ECG data (i.e. heart rate) according to the three detecting signals. The blood oxygen saturation and ECG data is formed a graphic continuous data by the MCU and then the data is transmitted to the smart terminal (such as mobile phones, tablet computer, servers or PC, etc.) in the wireless communication manner.

It should be note that the units in the above embodiments are divided only according the function logic, but are not limited to the above division, as long as the corresponding function can be achieved; Also, the specific names of the various functional units are only to facilitate distinguishing from each other, not intended to limit the scope of the present invention.

Further, it can be understood by those of ordinary skilled person in the that all or a part of the method steps of the above-described embodiments can be implemented by using a program to instruct relevant hardware, the corresponding program may be stored in a computer readable storage medium, such as ROM/RAM, disk or CD-ROM.

What described above are only preferred embodiments of the present disclosure but are not intended to limit the scope of the present disclosure, any modifications, equivalent replacements and improvements etc. made within the spirit and principle of the present invention, should be included in the protection scope of the present invention.

What is claimed is:

1. A portable detecting device with two electrodes, wherein the portable detecting device comprises:
    a main body of the portable detecting device: and
    a wrist strap,
    wherein the main body of the portable detecting device comprises:
        a front; and
        a back,
        wherein the front comprises a first lead electrode for detecting a finger signal; and the back comprises a second lead electrode detecting a wrist signal,
    wherein the first lead electrode comprises:
        a finger composite detecting probe; and
        an optical module,
    wherein the portable detecting device further comprises a detecting circuit, the detecting circuit comprising:
        an amplifier;
        a microcontroller unit; and
        a switching element,
    wherein a detecting signal of the optical module is connected to the microcontroller unit through the amplifier, and a detecting signal of the finger composite detecting probe and a detecting signal of the second lead electrode are connected to the microcontroller unit through the amplifier,
    wherein the detecting signal of the finger composite detecting probe or the detecting signal of the second lead electrode is directly connected to the microcontroller unit through both the amplifier and the switching element.

2. The portable detecting device according to claim 1, wherein the detecting circuit specifically comprises:
    a first amplifier, a second amplifier, a third amplifier, a microcontroller unit (MCU) and a field effect transistor, wherein:
    a negative terminal of the first amplifier is connected to an output terminal of the first amplifier, the output terminal of the first amplifier is connected to the MCU, a positive terminal of the first amplifier is connected to the detecting signal of the optical module;
    a negative terminal of the second amplifier is connected to an output terminal of the second amplifier, the output terminal of the second amplifier is connected to the MCU, a positive terminal of the second amplifier is connected to the detecting signal of the finger composite detecting probe; and
    a negative terminal of the third amplifier is connected to an output terminal of the third amplifier, the output terminal of the third amplifier is connected to the MCU, a positive terminal of the third amplifier is connected to the detecting signal of the second lead electrode; the detecting signal of the second lead electrode is connected to a drop terminal D of the field effect transistor, a source terminal S of the field effect transistor is connected to the ground, and a gate terminal G of the field effect transistor is connected to the MCU.

3. The portable detecting device according to claim 2, wherein the detecting circuit further comprises: a wireless transmitting module, the wireless transmitting module is connected to the MCU.

4. The portable detecting device according to claim 1, wherein the detecting circuit specifically comprises:
    a first amplifier, a second amplifier, a third amplifier, a microcontroller unit (MCU) and a field effect transistor, wherein:
    a negative terminal of the first amplifier is connected to an output terminal of the first amplifier, the output terminal of the first amplifier is connected to the MCU, a positive terminal of the first amplifier is connected to the detecting signal of the optical module;
    a negative terminal of the second amplifier is connected to an output terminal of the second amplifier, the output terminal of the second amplifier is connected to the MCU, a positive terminal of the second amplifier is connected to the detecting signal of the finger composite detecting probe; and
    a negative terminal of the third amplifier is connected to an output terminal of the third amplifier, the output terminal of the third amplifier is connected to the MCU, a positive terminal of the third amplifier is connected to a source terminal S of the field effect transistor; a drop terminal D of the field effect transistor is connected to the detecting signal of the second lead electrode, and a gate terminal G of the field effect transistor is connected to the MCU.

5. The portable detecting device according to claim 4, wherein the detecting circuit further comprises: a wireless transmitting module, the wireless transmitting module is connected to the MCU.

6. The portable detecting device according to claim 1, wherein the detecting circuit specifically comprises:
   a first amplifier, a second amplifier, a third amplifier, a microcontroller unit (MCU) and a field effect transistor, wherein:
   a negative terminal of the first amplifier is connected to an output terminal of the first amplifier, the output terminal of the first amplifier is connected to the MCU, a positive terminal of the first amplifier is connected to the detecting signal of the optical module;
   a negative terminal of the second amplifier is connected to an output terminal of the second amplifier, the output terminal of the second amplifier is connected to the MCU, a positive terminal of the second amplifier is connected to the detecting signal of the finger composite detecting probe; the detecting signal of the finger composite detecting probe is connected to a drop terminal D of the field effect transistor, a source terminal S of the field effect transistor is connected to the ground, and a gate terminal G of the field effect transistor is connected to the MCU; and
   a negative terminal of the third amplifier is connected to an output terminal of the third amplifier, the output terminal of the third amplifier is connected to the MCU, a positive terminal of the third amplifier is connected to the detecting signal of the second lead electrode.

7. The portable detecting device according to claim 6, wherein the detecting circuit further comprises: a wireless transmitting module, the wireless transmitting module is connected to the MCU.

8. The portable detecting device according to claim 1, wherein the detecting circuit specifically comprises:
   a first amplifier, a second amplifier, a third amplifier, a microcontroller unit (MCU) and a field effect transistor, wherein:
   a negative terminal of the first amplifier is connected to an output terminal of the first amplifier, the output terminal of the first amplifier is connected to the MCU, a positive terminal of the first amplifier is connected to the detecting signal of the optical module;
   a negative terminal of the second amplifier is connected to an output terminal of the second amplifier, the output terminal of the second amplifier is connected to the MCU, a positive terminal of the second amplifier is connected to a source terminal S of the field effect transistor, a drop terminal D of the field effect transistor is connected to the detecting signal of the finger composite detecting probe, and a gate terminal G of the field effect transistor is connected to the MCU; and
   a negative terminal of the third amplifier is connected to an output terminal of the third amplifier, the output terminal of the third amplifier is connected to the MCU, a positive terminal of the third amplifier is connected to the detecting signal of the second lead electrode.

9. The portable detecting device according to claim 8, wherein the detecting circuit further comprises: a wireless transmitting module, the wireless transmitting module is connected to the MCU.

\* \* \* \* \*